United States Patent [19]

Pappo et al.

[11] 4,161,480
[45] Jul. 17, 1979

[54] INTERMEDIATES FOR THE SYNTHESIS OF 4-DEMETHOXYDAUNORUBICIN

[75] Inventors: Raphael Pappo, Skokie; Robert B. Garland, Northbrook, both of Ill.

[73] Assignee: G. D. Searle & Co., Skokie, Ill.

[21] Appl. No.: 912,671

[22] Filed: Jun. 5, 1978

[51] Int. Cl.$^2$ ............ C07C 49/66; C07C 49/73; C07C 63/44
[52] U.S. Cl. .................................................. 260/365
[58] Field of Search ........................................ 260/365

[56] References Cited

U.S. PATENT DOCUMENTS 3,803,124  4/1974  Arcamone et al. ............ 260/210 AB
4,046,878  9/1977  Patelli et al. .......................... 424/180

OTHER PUBLICATIONS

*Cancer Treatment Reports*, vol. 60 (7), pp. 829–834, F. Arcamone et al. (1976).
*Can. Jol. Bio. Chem.*, vol. 51, pp. 466–467, C. M. Wong et al. 1973.
*Jol. Amer. Chem. Soc.*, vol. 98, pp. 1967–1969, A. S. Kende et al. 1976.
*Jol. Amer. Chem. Soc.*, vol. 98, pp. 1967–1971, T. H. Smith et al. 1976.

*Primary Examiner*—Allen B. Curtis
*Assistant Examiner*—Raymond Covington
*Attorney, Agent, or Firm*—Mary Jo Kanaday

[57] ABSTRACT

The present invention encompasses novel intermediates having the following structural formulas:

wherein X is hydrogen, methoxy, or hydroxy;

wherein X is hydrogen, methoxy, or hydroxy; and wherein X is hydrogen, methoxy, or hydroxy.

Compounds of the present invention are useful in synthesizing 4-demethoxydaunorubicin, daunorubicin, adriamycin, and carminomycin which are potent antitumor agents.

9 Claims, No Drawings

INTERMEDIATES FOR THE SYNTHESIS OF 4-DEMETHOXYDAUNORUBICIN

The present invention encompasses novel intermediates which are useful in preparing 4-demethoxydaunorubicin, daunorubicin, and adriamycin which are potent antitumor agents. The process is advantageous in that it is more amenable to large scale production of this class of antitumor agent.

4-Demethoxydaunorubicin is a glycoside formed from a tetracyclic aglycone, ($\pm$)-4-demethoxydaunomycinone, and an amino sugar, daunosamine. Daunorubicin is a glycoside formed from daunomycinone and daunosamine. Adriamycin is a glycoside formed from adriamycinone and daunosamine.

The synthesis of 4-demethoxydaunorubicin which is an analog of the known antibiotic daunorubicin is described in U.S. Pat. No. 4,046,878 and F. Arcamone, et. al., CANCER TREATMENT REPORTS, 60 (7):829-834 (1976) which also include experimental data showing its utility as a potent antitumor compound. Antitumor activity of ($\pm$)-4-demethoxydaunorubicin is also described in A. DiMarco, et. al., CANCER TREATMENT REPORTS, 61 (5):893-894 (1977). Other prior art related to the synthesis of daunomycinone, daunorubicin, adriamycinone, and adriamycin by methods which differ from the present invention is described in C. M. Wong, et. al., CAN. J. BIOCHEM., 51:466-467 (1973); A. S. Kende, et. al., J. AM. CHEM. SOC., 98:1967-1969 (1976); T. H. Smith, et.al., J. AM. CHEM. SOC., 98:1969-1971 (1976); A. S. Kende, et.al., TETRAHEDRON LETTERS, 40:3537-3540 (1977); F. Arcamone, et.al., CHIM. IND. (MILAN), 51:834 (1969), and U.S. Pat. No. 3,803,124.

The present invention differs from the prior art in that it utilizes novel trimethylsilyl or trialkylsilyl intermediates to afford a process which is more efficient and more amenable to large scale production.

It is the object of this invention to provide certain novel intermediates which are useful in the preparation of 4-demethoxydaunorubicin, daunorubicin, and adriamycin. These novel intermediates are converted into ($\pm$)-4-demethoxydaunomycinone or daunomycinone by means of the processes illustrated in Schemes A and B. ($\pm$)-4-Demethoxydaunomycinone may then be converted into 4-demethoxydaunomycin by methods described in U.S. Pat. No. 4,046,878. Daunomycinone may be used to prepare daunorubicin and adriamycin by methods described in Acton, et.al., J. MED. CHEM. 17:659-660 (1974).

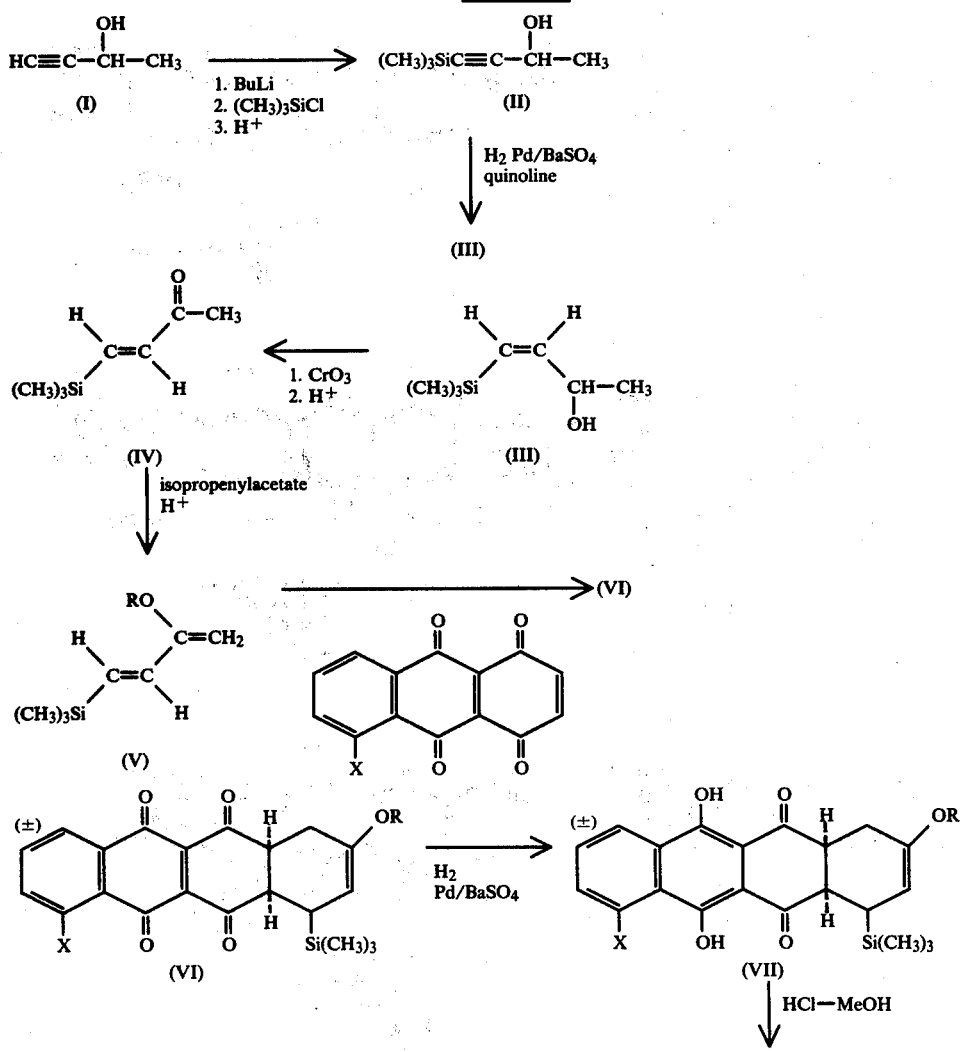

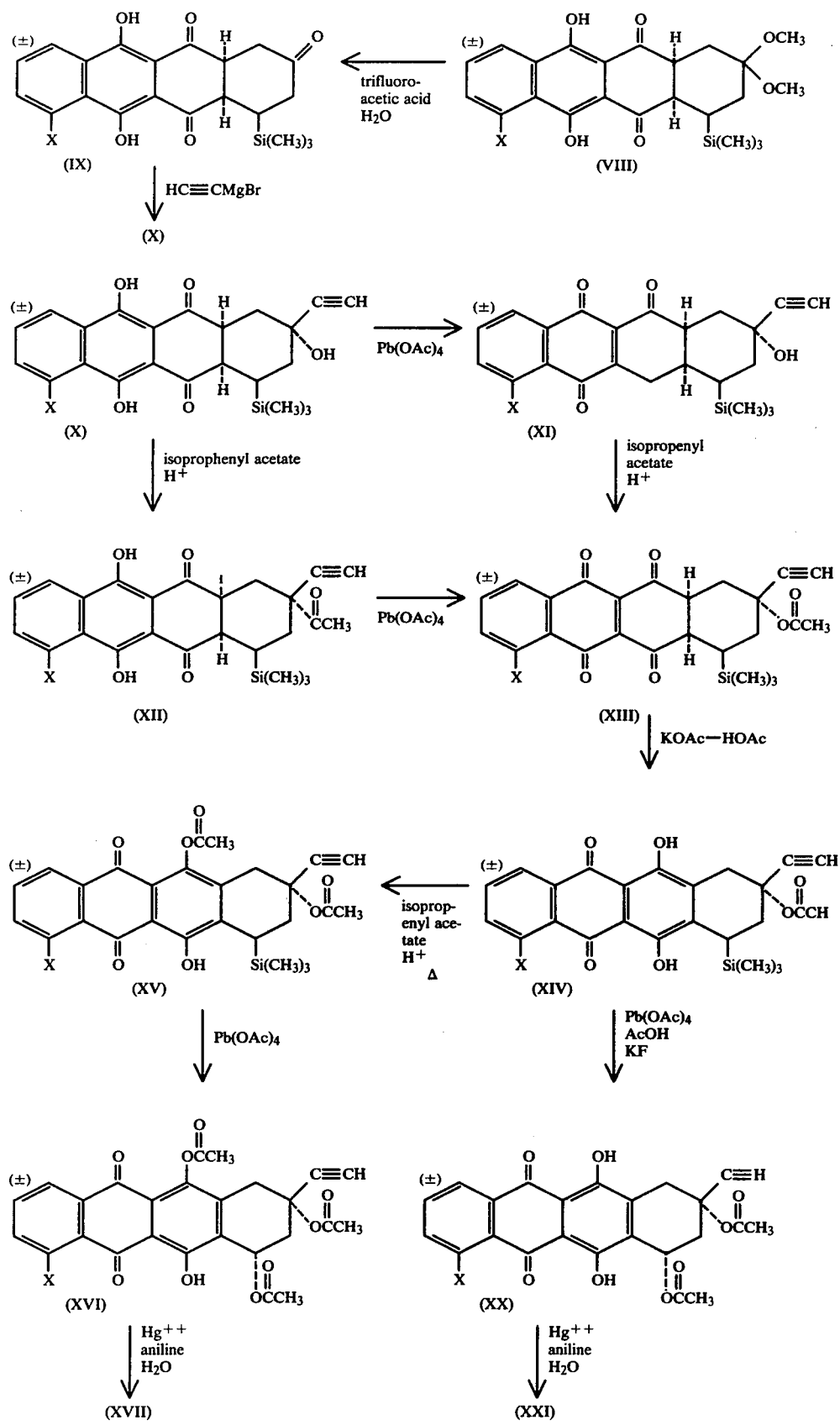

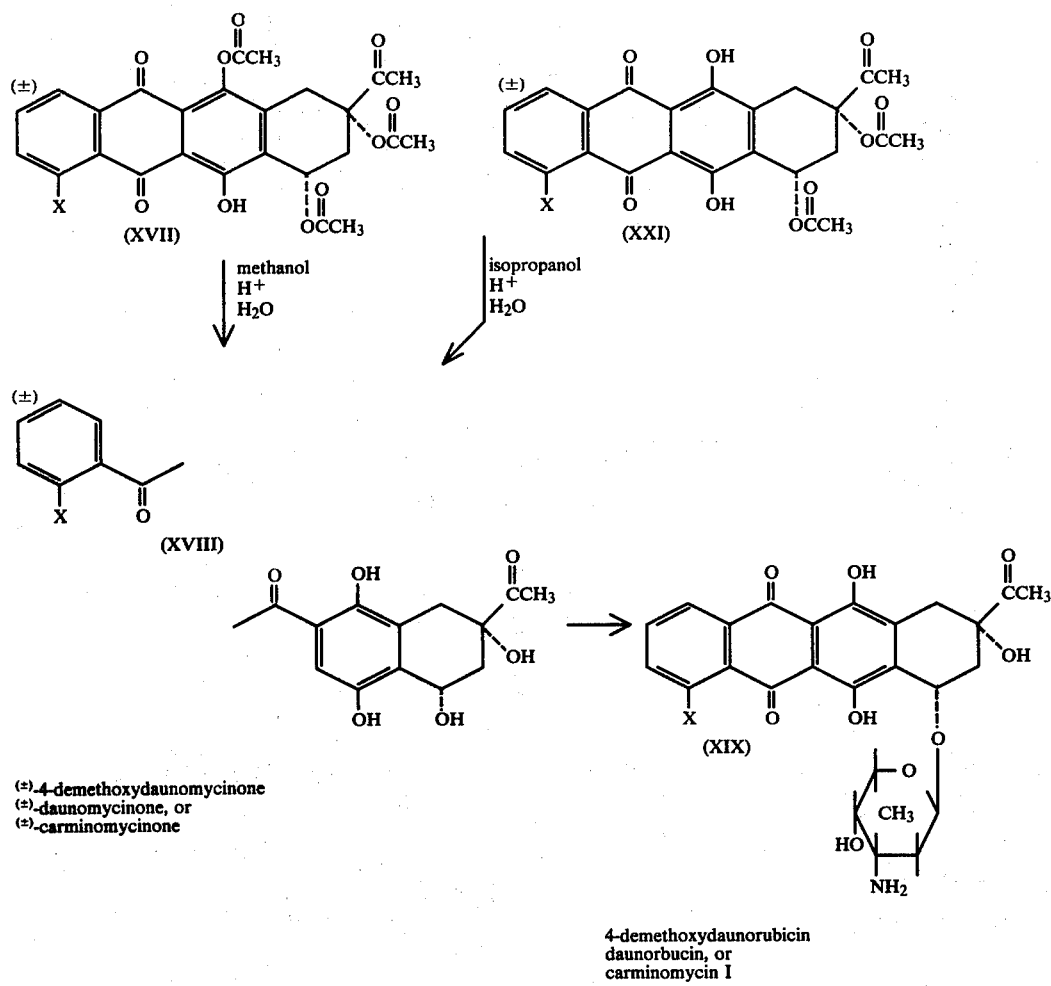
R = alkyl having 1-4 carbon atoms
  acyl having 1-5 carbon atoms
  trialkylsilyl wherein the alkyl radical
  has 1-4 carbon atoms.
X = hydrogen, methoxy, or hydroxy.
Scheme B
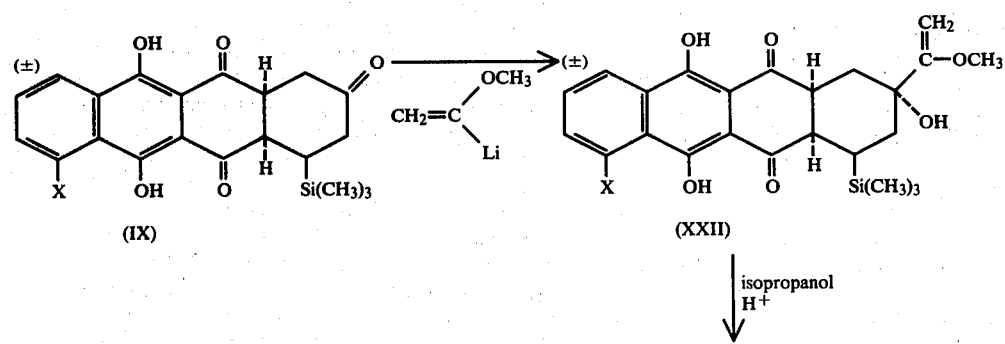

-continued
Scheme B

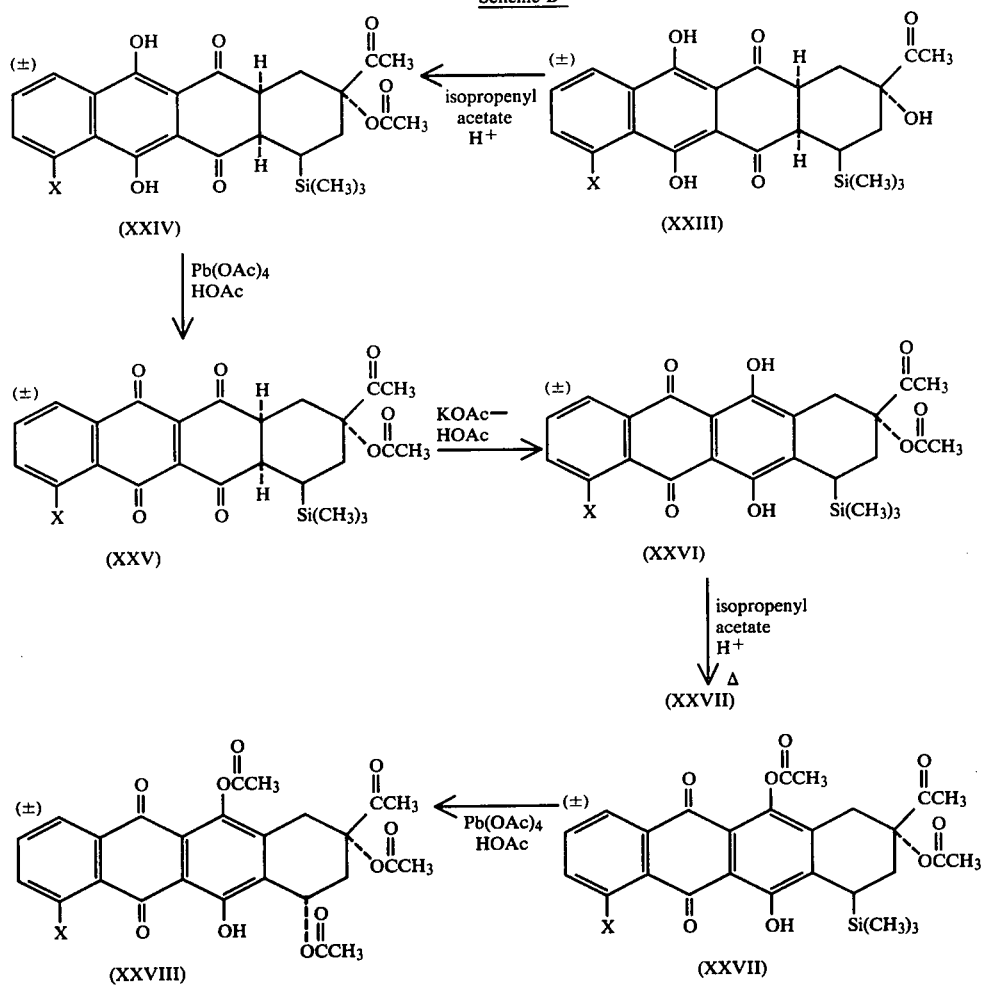

X = Hydrogen, methoxy, or hydroxy.

In a typical example, wherein R is acetyloxy and X is hydrogen, 3-butyne-2-ol (I) is reacted with butyl lithium and chlorotrimethylsilane and then with acid to give 4-(trimethylsilyl)-3-butyn-3-ol (II) which is hydrogenated in the presence of quinoline and benzene with palladium on barium sulfate as catalyst to give cis-4-(trimethylsilyl)-3-buten-2-ol (III). cis-4-(Trimethylsilyl)-3-buten-2-ol (III) is treated with Jones Reagent (a solution of chromic acid and sulfuric acid in water) at a temperature below 10° C. and the product is equilibrated with acid to give trans-4-(trimethylsilyl)-3-buten-2-one (IV). The preparation of this compound has been previously described [R. A. Felix, et. al. J. ORG. CHEM. 37, 2323 (1972), and H. G. Brook, CAN. J. CHEM. 51, 2024 (1973)]. trans-4-(Trimethylsilyl)-3-buten-2-one (IV) is reacted with isopropenyl acetate in the presence of acid to give trans-2-(acetyloxy)-4-(trimethylsilyl)-1,3-butadiene (V). trans-2-(Acetyloxy)-4-(trimethylsilyl)-1,3-butadiene (V) is reacted with quinizarinquinone to produce (±)-3-(acetyloxy)-1,4,4aβ,12aβ-tetrahydro-1α-(trimethylsilyl)-5,6,11,12-naphthacenetetrone (VI). The reaction is typically carried out at a temperature of 45°-50° C. over a period of 96 hours. Chemical reduction or hydrogenation of (±)-3-(acetyloxy)-1,4,4aβ,12aβ-tetrahydro-1α-(trimethylsilyl)-5,6,11,12-naphthacenetetrone (VI) using palladium on barium sulfate as catalyst provides (±)-3-(acetyloxy)-1,4,4aβ,12aβ-tetrahydro-6,11-dihydroxy-1α-(trimethylsilyl)-5,12-naphthacenedione (VII) which is refluxed with methanol and hydrochloric acid to give (±)-1,2,3,4,4aβ,12aβ-hexahydro-6,11-dihydroxy-3,3-dimethoxy-1α-(trimethylsilyl)-5,12-naphthacenedione (VIII) which is then reacted with trifluoroacetic acid and water to yield (±)-3,4,4aβ,12aβ-tetrahydro-6,11-dihydroxy-1α-(trimethylsilyl)-2,5,12(1H)-naphthacenetrione (IX). (±)-3,4,4aβ,12aβ-tetrahydro-6,11-dihydroxy-1α-(trimethylsilyl)-2,5,12(1H)-naphthacenetrione (IX) is converted to (±)-3-ethynyl-1,2,3,4,4aβ,12aβ-hexahydro-3β,6,11-trihydroxy-1α-(trimethylsilyl)-5,12-naphthacenedione (X) via a Grignard reaction. Compound X is stirred with isopropenyl acetate and acid for 20 hours at room temperature to give (±)-3β-(acetyloxy)-3-ethynyl-1,2,3,4,4aβ,12aβ-hexahydro-6,11-dihydroxy-1α-(trimethylsilyl)-5,12-naphthacenedione (XII) which is then oxidized with lead tetraacetate to provide (±)-3β-(acetyloxy)-3-ethynyl-1,2,3,4,4aβ,12aβ-hexahydro-1α-(trimethylsilyl)-5,6,11,12-naphthacenetetrone (XIII). Alternately, compound X is oxidized with lead tetraacetate to yield (±)-3-ethynyl-1,2,3,4,4aβ,12aβ-hexahydro-3β-hydroxy-1α-(trimethylsilyl)-5,6,11,12-naphthacenetetrone (XI) which is then heated with isopropenylacetate and acid to provide XIII. Heating XIII with potassium acetate and acetic acid yields trans-(±)-9-(acetyloxy)-9-ethynyl-7,8,9,10-tetrahydro-6,11-dihydroxy-1-(trimethylsilyl)-5,12-naphthacenedione (XIV) which is heated with isopropenyl acetate and acid to give trans-(±)-9,11-bis(acetyloxy)-9-ethynyl-7,8,9,10-tetrahydro-6-hydroxy-7-(trimethylsilyl)-5,12-naphthacenedione (XV). When XV is allowed to react with lead tetraacetate the trimethylsilyl group is replaced by an acetyloxy group to give cis-(±)-7,9,11-tris(acetyloxy)-9-ethynyl-7,8,9,10-tetrahydro-6-hydroxy-5,12-naphthacenedione (XVI) which when refluxed with mercuric chloride, aniline and water affords cis-(±)-9-acetyl-7,9,11-tris-(acetyloxy)-7,8,9,10-tetrahydro-6-hydroxy-5,12-naphthacenedione (XVII). Hydrolysis of the acetyloxy groups by reacting cis-(±)-9-acetyl-7,9,11-tris-(acetyloxy)-7,8,9,10-tetrahydro-6-hydroxy-5,12-naphthacenedione (XVII) with methanol and hydrochloric acid gives (±)-4-demethoxydaunomycinone (XVIII).

In an alternate route, XIV is reacted with lead tetraacetate and potassium fluoride in acetic acid then reduced to give cis-(±)-7,9-bis(acetyloxy)-9-ethynyl-7,8,9,10-tetrahydro-6,11-dihydroxy-5,12-naphthacenedione (XX). This reaction has the advantage of being stereospecific for the cis configuration so that it is not necessary to separate the cis isomer by chromatographic methods. XX is reacted with mercuric chloride, aniline and water to give cis-(±)-9-acetyl-7,9-bis-(acetyloxy)-7,8,9,10-tetrahydro-6,11-dihydroxy-5,12-naphthacenedione (XXI) which is then refluxed with isopropanol, water, and hydrochloric acid to give XVIII. (±)-4-demethoxydaunomycinone (XVIII) is converted to (±)-4-demethoxydaunorubicin (XIX) by methods described in U.S. Pat. No. 4,046,878.

When X is a methoxy group the final product is (±)-daunomycinone which may be converted to the known antitumor agent daunorubicin by methods described in E. A. Acton, et.al., J. MED. CHEM. 17(6), 659–660 (1974).

Scheme B illustrates an alternate route for converting (±)-3,4,4aβ,12aβ-tetrahydro-6,11-dihydroxy-1α-(trimethylsilyl)-2,5,12(1H)-naphthacenetrione (IX) into cis-(±)-9-acetyl-7,9,11-tris(acetyloxy)-7,8,9,10-tetrahydro-6-hydroxy-5,12-naphthacenedione (XVII). Methylvinyl ether is treated with tertiary butyl lithium in tetrahydrofuran and the product is allowed to react with (±)-3,4,4aβ,12aβ-tetrahydro-6,11-dihydroxy-1α-(trimethylsilyl)-2,5,12(1H)-naphthacenetrione (IX) to produce (±)-1,2,3,4,4aβ,12aβ-hexahydro-3β,6,11-trihydroxy-3-(1-methoxyethenyl)-1α-(trimethylsilyl)-5,12-naphthacenedione (XXII) which is hydrolyzed in aqueous isopropanol in the presence of hydrochloric acid to provide (±)-3-acetyl-1,2,3,4,4aβ,12aβ-hexahydro-3β,6,11-trihydroxy-1α-(trimethylsilyl)-5,12-naphthacenedione (XXIII). Mixing XXIII with isopropenyl acetate in the presence of acid and stirring at room temperature for 72 hours yields (±)-3-acetyl-3β-(acetyloxy)-2,3,4,5,5aβ,12aβ-hexahydro-6,11-dihydroxy-1α-(trimethylsilyl)-5,12-naphthacenedione (XXIV) which is reacted with lead tetraacetate in acetic acid to give (±)-3-acetyl-3β-(acetyloxy)-1,2,3,4,4aβ,12aβ-hexahydro-1α-(trimethylsilyl)-5,6,11,12-naphthacenetetrone (XXV). Warming XXV with potassium acetate in acetic acid gives trans-(±)-9-acetyl-9-(acetyloxy)-7,8,9,10-tetrahydro-6,11-dihydroxy-7-(trimethylsilyl)-5,12-naphthacenedione (XXVI). Heating XXVI with isopropenyl acetate in the presence of acid provides trans-(±)-9-acetyl-9,11-bis-(acetyloxy)-7,8,9,10-tetrahydro-6-hydroxy-7-(trimethylsilyl)-5,12-naphthacenedione (XXVII) which is allowed to react with lead tetraacetate in acetic acid for 2 hours at room temperature to give cis-(±)-9-acetyl-7,9,11-tris-(acetyloxy)-7,8,9,10-tetrahydro-6-hydroxy-5,12-naphthacenedione (XXVIII).

Those skilled in the art will recognize that other trialkylsilyl groups may be substituted for the trimethylsilyl group in the compounds of Scheme A and Scheme B by using conventional preparation techniques.

Thus the present invention encompasses intermediates of the formula

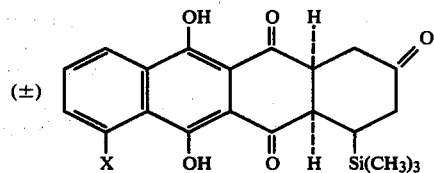

wherein X is hydrogen, methoxy, or hydroxy; intermediates of the formula

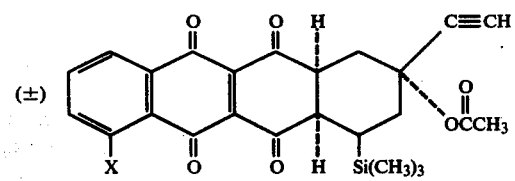

wherein X is hydrogen, methoxy, or hydroxy, and intermediates of the formula

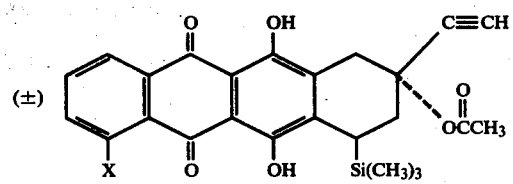

wherein X is hydrogen, methoxy, or hydroxy.

The following examples describe in detail the preparation of compounds utilizing the process of the present invention. It will be apparent to those skilled in the art that many modifications, both of materials and methods, may be practiced without departing from the purpose and intent of this disclosure. Throughout the examples hereinafter set forth temperatures are given in degrees Centigrade (°C.), and relative amounts in parts by weight and parts by volume is specified. The relationship between parts by weight and parts by volume is the same as that existing between grams and milliliters.

The Roman numerals used in the examples correspond to those used to describe compounds of Schemes A and B wherein X is hydrogen and R is acetyloxy.

EXAMPLE 1

A solution of 107.1 parts by weight of 3-butyne-2-ol (I) in 1000 parts by volume of dry ethyl ether is chilled to −50° C. (internal temperature) and 1390 parts by volume of 2.17 M n-butyl lithium in hexane is added over a 2 hour period. The internal temperature is allowed to reach 10° C. during the latter part of the addition to facilitate stirring. The mixture is then cooled again to −30° C. (internal) and 400 parts by volume of chlorotrimethylsilane in 200 parts by volume of ethyl ether is added over a 15 minute period. The mixture is allowed to warm slowly to room temperature overnight. After a brief period of reflux the mixture is again cooled to 25° C. and 100 parts by volume of water is added causing the internal temperature to rise to 37° C. After stirring for 1 hour, more water is added. The organic layer is separated and washed with 5% aqueous hydrochloric acid and water. The solution is dried over sodium sulfate, then concentrated to approximately 400 parts by volume. After adding 500 parts per volume of methanol and 200 parts per volume of 5% hydrochloric acid the solution is stirred at room temperature for one hour then diluted with 1000 parts per volume of water and extracted with ether. The ether extract is washed with water, dried over sodium sulfate and concentrated to afford 4-(trimethylsilyl)-3-butyn-2-ol (II) which distills at 49°-50° C./0.25 mm and has the following structural formula

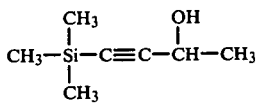

EXAMPLE 2

A solution of 94.15 parts by weight of 4-(trimethylsilyl)-3-butyn-2-ol (II) in 940 parts by volume of benzene and 4.7 parts by volume of quinoline is hydrogenated at a constant pressure of 2 p.s.i. in the presence of 9.4 parts by weight of 5% palladium on barium sulfate until one equivalent of hydrogen is consumed. The catalyst is removed and the solution is washed twice with 100 parts per volume of 5% aqueous hydrochloric acid and then with water. After drying over sodium sulfate, the solvent is removed and the residue is distilled at 33°-39° C./0.3 mm to give cis-4-(trimethylsilyl)-3-buten-2-ol (III) which has the following structural formula:

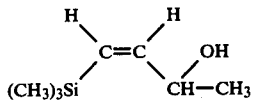

EXAMPLE 3

A solution of 174.6 parts by weight of cis-4-(trimethylsilyl)-3-buten-2-ol (III) in 2000 parts by volume of acetone is chilled to −10° C. and treated slowly with an excess (350 parts by volume) of Jones Reagent (a solution of chromic acid and sulfuric acid in water) while keeping the internal temperature below 10° C. The resulting precipitate is allowed to settle and the supernatant is decanted and concentrated on a rotary evaporator at 25° C. to remove much of the acetone. The precipitate is dissolved in water and the solution is extracted with ethyl ether. The ether extract is added to the acetone residue and the combined solutions are washed with water, then with 5% aqueous hydrochloric acid, and again with water. The ether extract is then dried over sodium sulfate and the ether removed by vacuum distillation. The residue is taken up in 500 parts by volume of isopropanol and 20 parts by volume of concentrated aqueous hydrochloric acid is added. The mixture is stored at room temperature for 18 hours then diluted with 1000 parts by volume of benzene and washed repeatedly with water. The washes are extracted with 500 parts by volume of benzene and dried over sodium sulfate to yield trans-4-(trimethylsilyl)-3-buten-2-one (IV) which has a boiling point of 165°-169° C. and is represented by the following structural formula

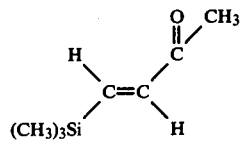

EXAMPLE 4

A mixture of 1.40 parts by weight of p-toluene sulfonic acid monohydrate and 100 parts by volume of benzene is distilled through a 15 cm. Vigreaux column until 75 parts per volume of distillate is collected. 100 Parts per volume isopropenylacetate is added to the reaction vessel and distillation is resumed until the boiling point reaches 92° C. After cooling to room temperature, 18.6 parts by weight of trans-4-(trimethylsilyl)-3-buten-2-one (IV) is added to the reaction vessel. The mixture is heated and distilled slowly with the temperature at the bottom of the column maintained at 85° C. for 20 hours. The reaction mixture is cooled then flash distilled, and the product is redistilled at 35°-37° C./0.3 mm to yield trans-2-(acetyloxy)-4-(trimethylsilyl)-1,3-butadiene (V) which has the following structural formula

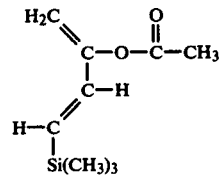

EXAMPLE 5

A solution of 29.9 parts by weight of 1,4,9,10-anthracenetetrone in 800 parts by volume of benzene is heated and about 50 parts by volume are removed by distillation. The remaining solution is then cooled under nitrogen to an internal temperature of 50° C. and 18.0 parts by weight of trans-2-(acetyloxy)-4-(trimethylsilyl)-1,3-butadiene (V) are added. The mixture is maintained at 45°-50° C. for 96 hours and then allowed to cool to room temperature with continued stirring overnight. 100 Parts by volume of cyclohexane is added and the mixture is chilled. The resulting solid is collected and washed with benzene then dried. The product is recrystallized from benzene to give (±)-3-(acetyloxy)-1,4,4a$\beta$,12a$\beta$-tetrahydro-1$\alpha$-(trimethylsilyl)-5,6,11,12-naphthacenetetrone (VI) which melts at 197°-200° C. and has the following structural formula

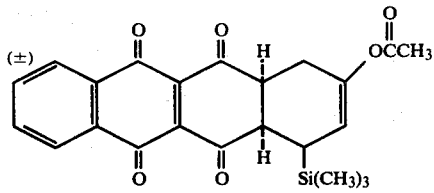

EXAMPLE 6

A solution of 19.3 parts by weight of (±)-3-(acetyloxy)-1,4,4aβ,12aβ-tetrahydro-1α-(trimethylsilyl)-5,6,11,12-naphthacenetetrone (VI) in 1300 parts by volume of tetrahydrofuran is hydrogenated over 1.93 parts by weight of 5% palladium on barium sulfate at a constant pressure of 2 p.s.i. for 2½ hours. The catalyst is removed and the filtrate concentrated to a small volume which is digested in 400 parts by volume of ethyl acetate. The resulting product is recrystallized from benzene-cyclohexane to give (±)-3-(acetyloxy)-1,4,4aβ,-12aβ-tetrahydro-6,11-dihydroxy-1α-(trimethylsilyl)-5,12-naphthacenedione (VII) which melts at 217°-225° C. (decomposition) and has the following structural formula

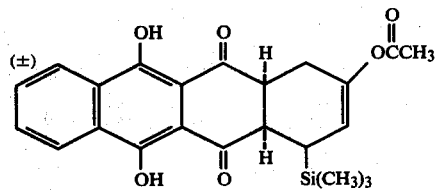

EXAMPLE 7

A suspension of 18.14 parts by weight of (±)-3-(acetyloxy)-1,4,4aβ,12aβ-tetrahydro-6,11-dihydroxy-1α-(trimethylsilyl)-5,12-naphthacenedione (VII) in 800 parts by volume of methanol, plus 10 parts by volume of concentrated hydrochloric acid is refluxed with vigorous stirring for 4 hours, then chilled well, filtered, and rinsed with cold methanol. The crude solid is recrystallized from methylene chloride-methanol to give (±)-1,2,3,4,4aβ,12aβ-hexahydro-6,11-dihydroxy-3,3-dimethoxy-1α-(trimethylsilyl)-5,12-naphthacenedione (VIII) which melts at 210°-211° C. and is represented by the following structural formula

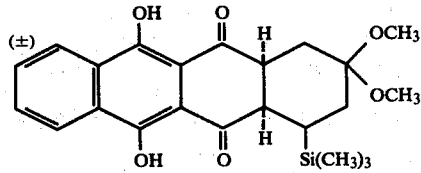

EXAMPLE 8

To a solution of 15.16 parts by weight of (±)-1,2,3,4,4aβ,12aβ-hexahydro-6,11-dihydroxy-3,3-dimethoxy-1α-(trimethylsilyl)-5,12-naphthacenedione (VIII) in 100 parts by volume of trifluoroacetic acid under nitrogen is added 20 parts by volume of water over a period of 1 hour, causing the solution to change from brown to pale yellow, with the formation of a solid yellow mass. 100 Parts by volume of water is added with mixing, and the solid is collected, washed with water, and dried. Recrystallization from benzene-ethyl ether gives (±)-3,4,4aβ,12aβ-tetrahydro-6,11-dihydroxy-4α-(trimethylsilyl)-2,5,12(1H)-naphthacenetrione (IX) which melts at 204°-207° C. (soft at 192° C.) and has the following structural formula

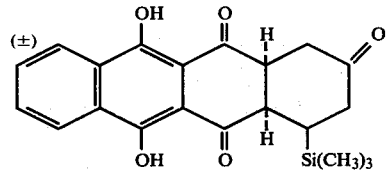

EXAMPLE 9

Purified acetylene is bubbled into a dry ice-cooled flask containing 150 parts per volume of freshly distilled tetrahydrofuran. After an increase of about 100 parts per volume is noted, 50 parts per volume of 2.53 M ethyl magnesium bromide in ether is added over a 10 minute period. The mixture is allowed to warm to 10° C., with acetylene still bubbling, then is cooled to −30° C. A solution of 11.5 parts by weight of (±)-3,4,4aβ,-12aβ-tetrahydro-6,11-dihydroxy-1α-(trimethylsilyl)-2,5,12(1H)-naphthacenetrione (IX) in a total of 450 parts per volume tetrahydrofuran is added with stirring. The mixture is held at −20° C. for 30 minutes, then the temperature is allowed to rise to 0° C. and held there for another 30 minutes. 50 Parts per volume of cold saturated ammonium chloride is added, followed by 150 parts per volume of 50% aqueous HCl, and then 300 parts per volume of water and nitrogen is bubbled through the mixture overnight. The solid which separates is filtered, washed with water, and dried. 12.6 Parts by weight of the solid is dissolved in methylene chloride, the solution is concentrated to about 75 parts per volume, and 150 parts per volume of cyclohexane is added. The resulting precipitate is recovered by filtration and recrystallized from ethyl ether-hexane to give (±)-3-ethynyl-1,2,3,4,4aβ,12aβ-hexahydro-3β,6,11-trihydroxy-1α-(trimethylsilyl)-5,12-naphthacenedione (X) which melts at 206°-208° C. and has the following structural formula:

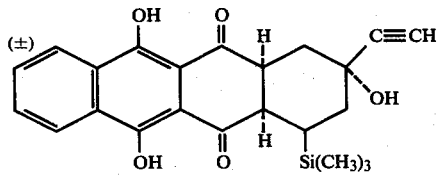

Concentration of the mother liquors and recrystallization of the precipitate from benzene-cyclohexane gives (±)-3-ethynyl-1,2,3,4,4aβ,12aβ-hexahydro-3α,6,11-trihydroxy-1α-(trimethylsilyl)-5,12-naphthacenedione which melts at 229°-231° C. and has the following structural formula

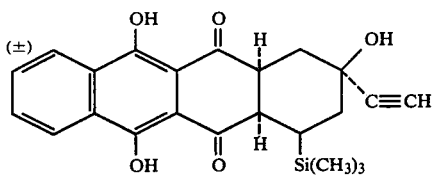

Chromatography of the mother liquors (dry column 60 parts by weight of neutral silicic acid, 100–200 mesh developed with ethylacetate-benzene) gives partial separation of the above compounds. The first eluate is recrystallized from methylene chloride-cyclohexane to give (±)-3-ethynyl-1,2,3,4,4aβ,12aβ-hexahydro-3β,6,11-trihydroxy-1α-(trimethylsilyl)-5,12-naphthacenedione (X) which melts at 204°–206° C. The later fractions are recrystallized from benzene-cyclohexane to give (±)-3-ethynyl-1,2,3,4,4aβ,12aβ-hexahydro-3α,6,11-trihydroxy-1α-(trimethylsilyl)-5,12-naphthacenedione which melts at 229°–231° C.

EXAMPLE 10

To a suspension of 12.26 parts by weight of (±)-3-ethynyl-1,2,3,4,4aβ,12aβ-hexahydro-3β,6,11-trihydroxy-1α-(trimethylsilyl)-5,12-naphthacenedione (X) in 100 parts per volume of acetic acid is added 16.5 parts by weight of approximately 85% lead tetraacetate. The solution is allowed to stand for 30 minutes at room temperature, then 100 parts per volume of water is added slowly with vigorous stirring. The mixture is chilled and filtered. The solid collected on the filter is washed with water and dried under high vacuum to give (±)-3-ethynyl-1,2,3,4,4aβ,12aβ-hexahydro-3β-hydroxy-1α-(trimethylsilyl)-5,6,11,12-naphthacenetetrone (XI) which melts at 183°–187° C. and has the following structural formula

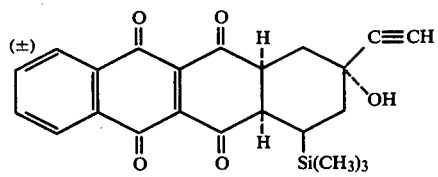

EXAMPLE 11

To a suspension of 1.0 part per weight of (±)-3-ethynyl-1,2,3,4,4aβ,12aβ-hexahydro-3β,6,11-trihydroxy-1α-(trimethylsilyl)-5,12-naphthacenedione (X) in 15 parts per volume of isopropenyl acetate is added 0.05 part by weight of p-toluenesulfonic acid hydrate. The mixture is stirred at room temperature for 20 hours, then concentrated under a stream of nitrogen to about 5 parts per volume. After adding 20 parts per volume of ethyl ether, the solid which forms is collected and washed with ether. The crude product is recrystallized from methylene chloride-ethyl ether to yield (±)-3β-(acetyloxy)-3-ethynyl-1,2,3,4,4aβ,12aβ-hexahydro-6,11-dihydroxy-1α-(trimethylsilyl)-5,12-naphthacenedione (XII) melting at 211°–213° C. and having the following structural formula

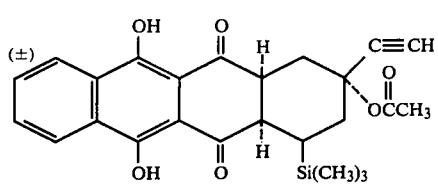

The combined mother liquors are concentrated to a small volume, passed through a 10 parts per weight neutral silicic acid column in methylene chloride and crystallized. Recrystallization from benzene-cyclohexane gives a sample of the above product, having a melting point of 213°–214° C.

EXAMPLE 12

(A) A suspension of 10.26 parts by weight of (±)-3-ethynyl-1,2,3,4,4aβ,12aβ-hexahydro-3β-hydroxy-1α-(trimethylsilyl)-5,6,11,12-naphthacenetetrone (XI) and 0.075 part by weight of p-toluenesulfonic acid hydrate in 50 parts by volume of isopropenyl acetate is heated for 3 hours in a 60° water bath (solution is not complete but the solid becomes lighter in color). The mixture is cooled to room temperature over a two-hour period, then diluted with 50 parts by volume of ethyl ether. The crude solid is collected, washed with ethyl ether and recrystallized from methylene chloride-ethyl ether to yield (±)-3β-(acetyloxy)-3-ethynyl-1,2,3,4,4aβ,12aβ-hexahydro-1α-(trimethylsilyl)-5,6,11,12-naphthacenetetrone (XIII) which melts at 206°–208° C. (decomposition) and has the following structural formula:

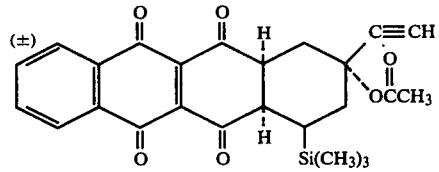

(B) To a suspension of 0.67 part by weight of (±)-3β-(acetyloxy)-3-ethynyl-1,2,3,4,4aβ,12aβ-hexahydro-6,11-dihydroxy-1α-(trimethylsilyl)-5,12-naphthacenedione (XII) in 10 parts per volume of acetic acid is added 1.0 part by weight of approximately 85% lead tetraacetate, causing the yellow solid to dissolve and a pink solid to precipitate. The mixture is allowed to stand for 30 minutes, then 25 parts per volume of water is added. The solid is collected, washed with water, and dried. Recrystallization from methylene chloride-ethyl ether gives (±)-3β-(acetyloxy)-3-ethynyl-1,2,3,4,4aβ,12aβ-hexahydro-1α-(trimethylsilyl)-5,6,11,12-naphthacenetetrone (XIII) which melts at 213°–215° C. (decomposition) and has the following structural formula:

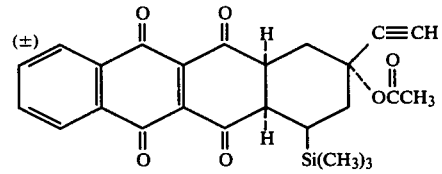

EXAMPLE 13

To a solution of 4.6 parts by weight of (±)-3β-(acetyloxy)-3-ethynyl-1,2,3,4,4aβ,12aβ-hexahydro-1α-

(trimethylsilyl)-5,6,11,12-naphthacenetetrone (XIII) in 50 parts per volume of acetic acid at 95° C. is added 5 parts by volume of acetic acid saturated with potassium acetate. The mixture is held at 95° C. for 3 hours, then allowed to cool to room temperature and diluted with 5 parts per volume of water. The solid is removed by filtration, washed with water, and dried. Recrystallization from methylene chloride-ethyl ether gives trans-(±)-9-(acetyloxy)-9-ethynyl-7,8,9,10-tetrahydro-6,11-dihydroxy-7-(trimethylsilyl)-5,12-naphthacenedione (XIV) which melts at 204°-206° C. and has the following structural formula

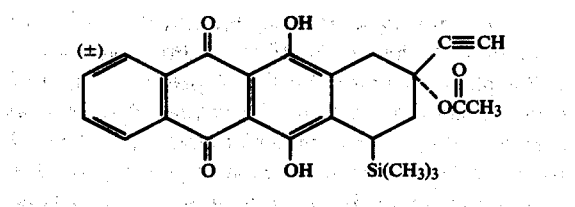

EXAMPLE 14

A suspension of 20.02 parts by weight of trans-(±)-9-(acetyloxy)-9-ethynyl-7,8,9,10-tetrahydro-6,11-dihydroxy-7-(trimethylsilyl)-5,12-naphthacenedione (XIV) and 1.0 part by weight of p-toluenesulfonic acid monohydrate in 200 parts by volume of isopropenyl acetate is heated under a 20 centimeter Vigreaux column and slowly distilled at 60°-80° C. for 3 hours, then at 80°-95° C. for 1 hour until about 30 parts per volume of distillate is collected. The contents of the reaction vessel are cooled to room temperature, with the formation of a thick solid. The reaction mixture is diluted with 50 parts per volume of ethyl ether and chilled, and the solid is collected and washed with ethyl ether. Recrystallization from methylene chloride-ether gives trans-(±)-9,11-bis(acetyloxy)-9-ethynyl-7,8,9,10-tetrahydro-6-hydroxy-7-(trimethylsilyl)-5,12-naphthacenedione (XV) which melts at 181°-182° C. and has the following structural formula

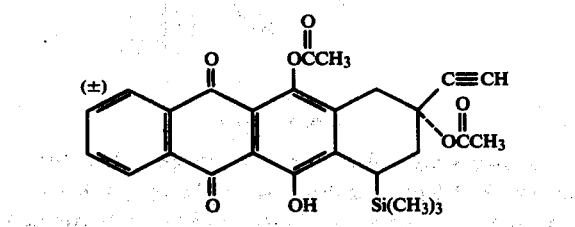

The combined mother liquors are stripped of most of the ether, diluted with methylene chloride, washed with water and dried over sodium sulfate. After concentrating to dryness, the residue is chromatographed on a dry column of 60 parts of neutral silic acid, 100-200 mesh. (The material is dissolved in benzene, then developed with 200 parts per volume of benzene, 1%, 2%, and 5% ethyl acetate in benzene and the fractions are collected by color bands).

The first fraction is crystallized from methylene chloride-ether to yield the starting material.

The second fraction is crystallized from methylene chloride-ethyl ether to yield trans-(±)-9,11-bis-(acetyloxy)-9-ethynyl-7,8,9,10-tetrahydro-6-hydroxy-7-(trimethylsilyl)-5,12-naphthacenedione (XV) melting at 179°-182° C. and having the following structural formula

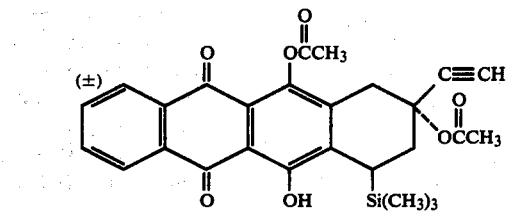

The third fraction is crystallized from ethyl ether-hexane to yield trans-(±)-6,9,11-tris(acetyloxy)-9-ethynyl-7,8,9,10-tetrahydro-7-(trimethylsilyl)-5,12-naphthacenedione which melts at 205°-207° C. and has the following structural formula

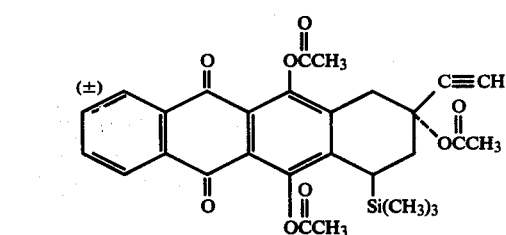

EXAMPLE 15

To a solution of 14.3 parts by weight of dried lead tetraacetate in 500 parts by volume of acetic acid is added 1.0 part by volume of water followed by 14.65 parts by weight of trans-(±)-9,11-bis(acetyloxy)-9-ethynyl-7,8,9,10-tetrahydro-6-hydroxy-7-(trimethylsilyl)-5,12-naphthacenedione (XV). The mixture is stirred at room temperature for 4 hours, then heated to 40° C. for about 30 minutes until solution is complete. The solution is held at room temperature for 2 hours, then 1.0 part per volume of water is added and stirring is continued for another 2 hours. 50 Parts per volume of water is added, and the solution is stirred overnight while remaining at room temperature. The resulting precipitate is collected, washed with 90% acetic acid and digested in 200 parts per volume of hot acetic acid. 50 Parts per volume of water is added and the solution is cooled. The resulting solid is collected, washed with water, dried and chromatographed on 80 parts by weight of neutral silicic acid, 100-200 mesh developing with 5% ethyl acetate in methylene chloride. The major fraction is crystallized from benzene-cyclohexane to give cis-(±)-7,9,11-tris(acetyloxy)-9-ethynyl-7,8,9,10-tetrahydro-6-hydroxy-5,12-naphthacenedione (XVI) which melts at 233°-235° C. (decomposition) and has the following structural formula

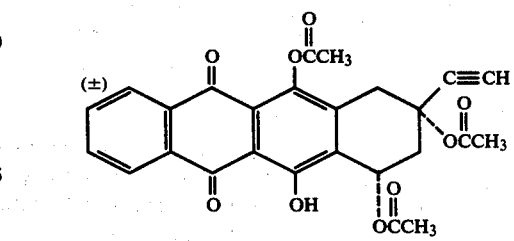

The various acetic acid mother liquors are concentrated to about 100 parts by volume and diluted with 200 parts by volume of water. The crude solid which results is filtered, washed with water, dried and chromatographed as before. The main fraction when crystallized from benzenecyclohexane gives a mixture of isomers melting at 220°-224° C. (decomposition) consisting of about 40% of cis-(±)-7,9,11-tris(acetyloxy)-9-ethynyl-7,8,9,10-tetrahydro-6-hydroxy-5,12-naphthacenedione (XVI) having the following structural formula

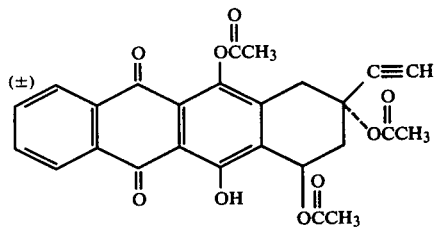

and about 60% of trans-(±)-7,9,11-tris(acetyloxy)-9-ethynyl-7,8,9,10-tetrahydro-6-hydroxy-5,12-naphthacenedione having the following structural formula:

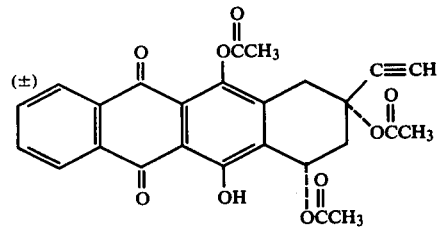

The filtrates and minor (slower) fractions from chromatograms are combined and re-chromatographed on 60 parts by weight of neutral silic acid 100-200 mesh developing with 600 parts by volume of 5% ethyl acetate in benzene, followed by 200 parts by volume of 10% ethyl acetate in benzene, then 200 parts by volume of 20% ethyl acetate in benzene.

The first fraction is crystallized from benzenecyclohexane to yield a mixture of the above cis and trans isomers melting at 224°-230° C. (decomposition).

The second fraction is crystallized from benzene-ethyl ether to give cis-(±)-9,11-bis(acetyloxy)-9-ethynyl-7,8,9,10-tetrahydro-6,7-dihydroxy-5,12-naphthacenedione which melts at 233°-235° C. (decomposition) and has the following structural formula:

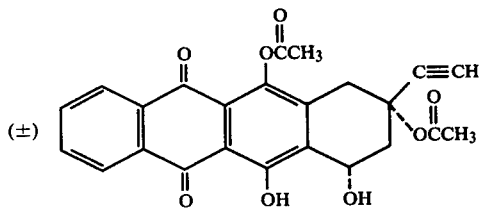

The third fraction is crystallized from benzene to give cis-(±)-7,11-bis(acetyloxy)-9-ethynyl-7,8,9,10-tetrahydro-6,9-dihydroxy-5,12-naphthacenedione which melts at 224°-226° C. and has the following structural formula

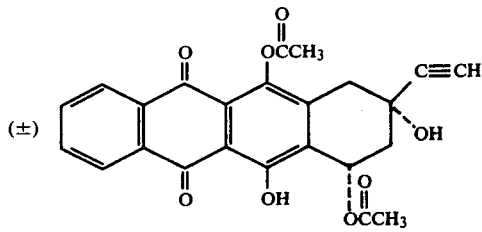

EXAMPLE 16

A mixture of 0.4 part by weight of cis-(±)-7,9,11-tris-(acetyloxy)-9-ethynyl-7,8,9,10-tetrahydro-6-hydroxy-5,12-naphthacenedione (XVI), 0.58 part by weight of mercuric chloride, 0.10 part by volume of aniline, 24 parts by volume of benzene and 4.8 parts by volume of water is refluxed with vigorous stirring for 5 hours. The resulting suspension is filtered to yield a mercuric complex of the product which is suspended in 300 parts by volume of methylene chloride. Hydrogen sulfide is bubbled through the suspension. The mercuric sulfide which forms is removed by filtration and the filtrate is concentrated to dryness. The residue is chromatographed on a 10 parts by weight neutral silicic acid 100-200 mesh column developed with 5% ethyl acetate in methylene chloride. The main fraction is crystallized from benzene-ethyl ether to yield cis-(±)-9-acetyl-7,9,11-tris(acetyloxy)-7,8,9,10-tetrahydro-6-hydroxy-5,12-naphthacenedione (XVII) which melts at 220°-223° C. and has the following structural formula

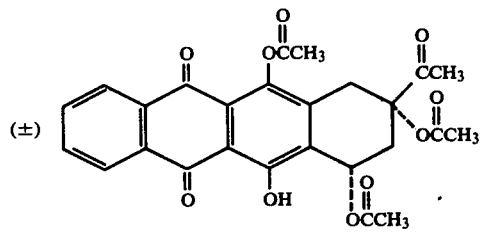

EXAMPLE 17

A suspension of 0.156 part by weight of cis-(±)-9-acetyl-7,9,11-tris(acetyloxy)-7,8,9,10-tetrahydro-6-hydroxy-5,12-naphthacenedione (XVII) in 40 parts by volume of methanol, 10 parts by volume of water and 1 part by volume of concentrated aqueous hydrochloric acid is refluxed for 40 hours. The resulting monohydrate which precipitates as red crystals is removed by filtration. The anhydrous form of the product is obtained by refluxing a sample of the monohydrate in benzene under a Dean-Stark trap. The resulting solution is filtered and the filtrate is concentrated to yield a small residue. The residue is diluted with ethyl ether and the resulting solid is collected by filtration to give cis-(±)-9-acetyl-7,8,9,10-tetrahydro-6,7,9,11-tetrahydroxy-5,12-naphthacenedione (XVIII) also known as (±)-4-demethoxydaunomycinone which melts at 194°-196° C. and has the following structural formula (±) 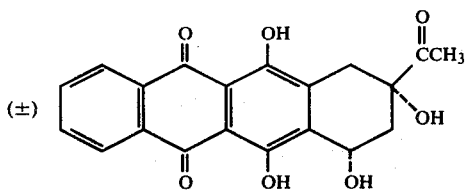

(±) 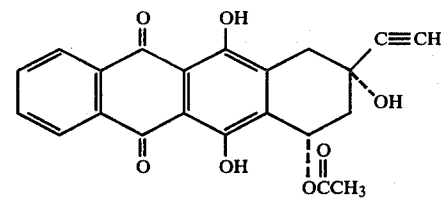

EXAMPLE 18

A suspension of 1.5 parts by weight of trans-(±)-9-(acetyloxy)-9-ethynyl-7,8,9,10-tetrahydro-6,11-dihydroxy-7-(trimethylsilyl)-5,12-naphthacenedione (XIV) and 3.1 parts by weight of lead tetraacetate in 25 parts by volume of acetic acid is stirred for 3 hours (until all the red solid dissolves). Addition of 0.9 part by weight of potassium fluoride gives a thick white precipitate (lead II fluoride). The mixture is stirred for 18 hours at room temperature then diluted with 200 parts by volume of methylene chloride. The white precipitate is removed by filtration. To the filtrate is added 1 part by weight of sodium bisulfite, then 100 parts by volume of water is added slowly with stirring. The organic layer is separated and washed with water and dried over sodium sulfate. After the solvent is removed, the residue is triturated with ethyl ether then recrystallized from methylene chloride-ethyl ether to yield cis-(±)-7,9-bis-(acetyloxy)-9-ethynyl-7,8,9,10-tetrahydro-6,11-dihydroxy-5,12-naphthacenedione (XX) which melts at 265°-266° C. and has the following structural formula

EXAMPLE 19

A suspension of 1.066 parts by weight of cis-(±)-7,9-bis(acetyloxy)-9-ethynyl-7,8,9,10-tetrahydro-6,11-dihydroxy-5,12-naphthacenedione (XX) and 1.50 parts by weight of mercuric chloride in 0.26 parts by volume of aniline, 18.0 parts by volume of water, and 90.0 parts by volume of benzene is refluxed with vigorous stirring for 12 hours and then allowed to cool to room temperature.

The solid is collected by filtration. The organic layer of the filtrate is separated and evaporated to dryness. The residue is combined with the solid and suspended in 800 parts by volume of methylene chloride. 50 Parts by volume of 10% aqueous hydrochloric acid is added and the mixture is stirred until solution is complete. The methylene chloride layer is separated, treated with hydrogen sulfide and filtered. The filtrate is concentrated and the residue is crystallized from methylene chloride-ethyl ether to give cis-(±)-9-acetyl-7,9-bis(acetyloxy)-7,8,9,10-tetrahydro-6,11-dihydroxy-5,12-naphthacenedione (XXI) which melts at 243°-245° C. and has the following structural formula (±) 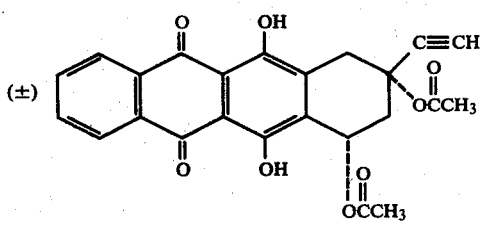

(±) 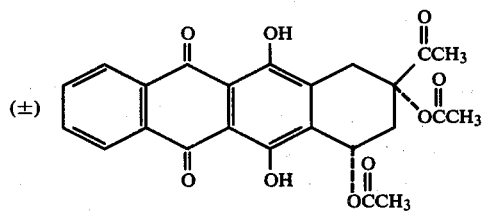

The combined mother liquors are chromatographed on 40 parts by weight of neutral silicic acid, developing with 1% ethyl acetate in methylene chloride. The first fraction eluted is crystallized from methylene chloride-ethyl ether to yield the above product.

The second fraction is crystallized from methylene chloride-ethyl ether to yield cis-(±)-9-(acetyloxy)-9-ethynyl-7,8,9,10-tetrahydro-6,7,11-trihydroxy-5,12-naphthacenedione which melts at 245°-248° C. and has the following structural formula

EXAMPLE 20

A suspension of 0.082 parts by weight of cis-(±)-9-acetyl-7,9-bis(acetyloxy)-7,8,9,10-tetrahydro-6,11-dihydroxy-5,12-naphthacenedione (XXI) in 40 parts by volume of isopropanol, 5 parts by volume of water, and 1 part by volume of concentrated hydrochloric acid is refluxed for 48 hours, then diluted with 10 parts by volume of water and distilled until about 20 parts by volume remain in the reaction vessel. The mixture is allowed to cool and the solid which forms is collected, washed with water, and dried then recrystallized from benzene-ethyl ether to give cis-(±)-9-acetyl-7,8,9,10-tetrahydro-6,7,9,11-tetrahydroxy-5,12-naphthacenedione (XVIII) which melts at 197°-200° C. and has the following structural formula (±) 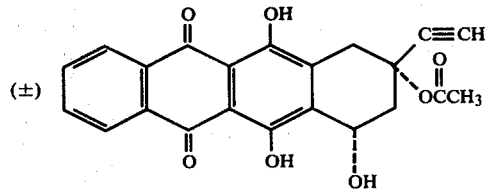

The third fraction is evaporated to provide crude cis-(±)-7-(acetyloxy)-9-ethynyl-7,8,9,10-tetrahydro-6,9,11-trihydroxy-5,12-naphthacenedione which has the following structural formula (±) 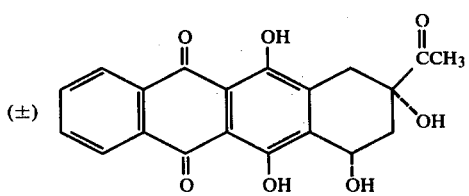

EXAMPLE 21

Substituting 5-methoxy-1,4,9,10-anthracenetetrone for the 1,4,9,10-anthracenetetrone in Example 5 and substantially repeating procedures described in Examples 5 through 20 gives cis-(±)-9-acetyl-4-methoxy-7,8,9,10-tetrahydro-6,7,9,11-tetrahydroxy-5,12-naphthacenedione also known as (±)-daunomycinone which has the following structural formula

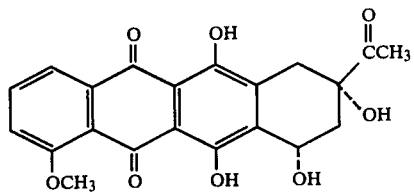

EXAMPLE 22

A solution of 0.7 part by weight of methyl vinyl ether in 12 parts by volume of dry tetrahydrofuran is cooled to −55° C. and three parts by volume of 1.8 M tertiary butyl lithium in pentane is added. The resulting suspension is allowed to warm until solution is complete and is then added to a cold (−30° C.) solution of 0.382 part by weight of (±)-3,4,4aβ,12aβ-tetrahydro-6,11-dihydroxy-1α-(trimethylsilyl)-2,5,12(1H)-naphthacenetrione (IX) in 20 ml of dry tetrahydrofuran. The reaction mixture is allowed to warm slowly to about 0° C. and is poured onto 200 ml of 20% aqueous ammonium chloride solution. The mixture is extracted with methylene chloride and the extracts are washed with water and dried over sodium sulfate. Removal of solvents leaves a brown oil which is crude (±)-1,2,3,4,4aβ,12aβ-hexahydro-3β,6,11-trihydroxy-3-(1-methoxyethenyl)-1α-(trimethylsilyl)-5,12-naphthacenedione (XXII) which has the following structural formula

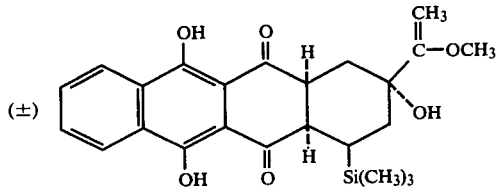

This crude material is dissolved in 40 ml of isopropanol and 10 ml of 0.1 N hydrochloric acid is added. After stirring for 1 hour at room temperature, the mixture is diluted with water and the crude product is collected and dried. Chromatographic purification on neutral silicic acid developing with 10% ethyl acetate in benzene produces a main fraction consisting of about 70% of (±)-3-acetyl-1,2,3,4,4aβ,12aβ-hexahydro-3β,6,11-trihydroxy-1α-(trimethylsilyl)-5,12-naphthacenedione (XXIII) which has the following structural formula

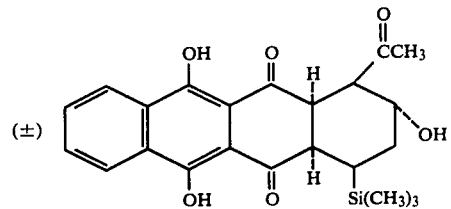

and about 30% of (±)-3-acetyl-1,2,3,4,4aβ,12aβ-hexahydro-3α,6,11-trihydroxy-1α-(trimethylsilyl)-5,12-naphthacenedione which has the following structural formula

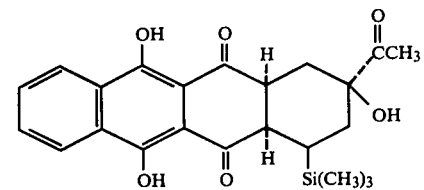

EXAMPLE 23

A suspension of 0.130 part by weight of crude (±)-3-acetyl-1,2,3,4,4aβ,12aβ-hexahydro-3β,6,11-trihydroxy-1α-(trimethylsilyl)-5,12-naphthacenedione (XXIII) in 10 parts by volume of isopropenyl acetate and 0.060 part by weight of p-toluenesulfonic acid monohydrate is stirred for 72 hours at room temperature, with solution gradually occurring. Following the addition of 0.100 part by weight of sodium bicarbonate the mixture is diluted with water and extracted with methylene chloride. The extract is evaporated to dryness and the residue is purified by chromatography on neutral silicic acid developing with 2% ethyl acetate in benzene. The main fraction is crystallized from methylene chloride ethyl ether to yield (±)-3-acetyl-3β-(acetyloxy)-1,2,3,4,4aβ,12aβ-hexahydro-6,11-dihydroxy-1α-(trimethylsilyl)-5,12-naphthacenedione (XXIV) which melts at 238°–242° C. and has the following structural formula

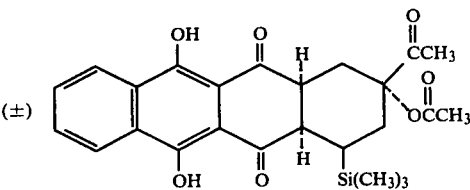

The mother liquors contain additional amounts of this compound mixed with the isomeric (±)-3-acetyl-3α-(acetyloxy)-1,2,3,4,4aβ,12aβ-hexahydro-6,11-dihydroxy-1α-(trimethylsilyl)-5,12-naphthacenedione which has the following structural formula:

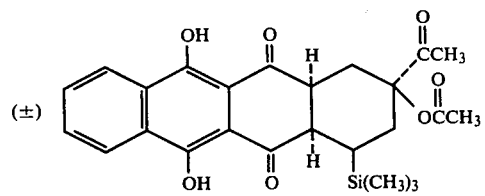

EXAMPLE 24

To a suspension of 0.340 part by weight of (±)-3-acetyl-3β-(acetyloxy)-1,2,3,4,4aβ,12aβ-hexahydro-6,11-dihydroxy-1α-(trimethylsilyl)-5,12-naphthacenedione (XXIV) in 10 parts by volume of acetic acid is added 0.500 part by weight of lead tetraacetate. The mixture is stirred vigorously for 30 minutes during which time the yellow solid dissolves and a pink solid separates. After diluting the mixture with 10 parts by volume of water the solid is collected, washed with water and dried to yield crude (±)-3-acetyl-3β-(acetyloxy)-1,2,3,4,4aβ,12aβ-hexahydro-1α-(trimethylsilyl)-5,6,11,12-naphthacenetetrone (XXV) which has the following structural formula

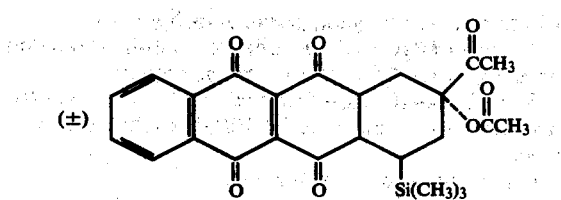

To this material is added 10 parts by volume of acetic acid, the mixture is heated to 90° C. and 1 part by volume of a saturated solution of potassium acetate in acetic acid is added. After 3 hours at 90° C. the mixture is allowed to cool and is diluted with 10 parts by volume of water. The solid is collected, washed with water and dried to yield crude trans-(±)-9-acetyl-9-(acetyloxy)-7,8,9,10-tetrahydro-6,11-dihydroxy-7-(trimethylsilyl)-5,12-naphthacenedione (XXVI) which has the following structural formula

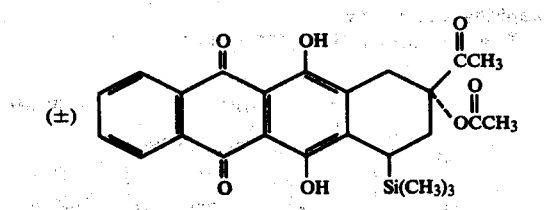

This material together with 0.001 part by weight of p-toluenesulfonic acid monohydrate is heated in 25 parts by volume of isopropenyl acetate with slow distillation of about 10 parts by volume over a 4 hour period. The mixture is cooled to room temperature and 0.100 part by weight of sodium bicarbonate is added followed by 20 parts by volume of water. The resulting suspension is extracted with methylene chloride. After chromatographic purification on neutral silicic acid developing with 1% ethyl acetate in methylene chloride, the main fraction on trituration with ethyl ether gives trans-(±)-9-acetyl-9,11-bis(acetyloxy)-7,8,9,10-tetrahydro-6-hydroxy-7-(trimethylsilyl)-5,12-naphthacenedione (XXVII) which has the following structural formula

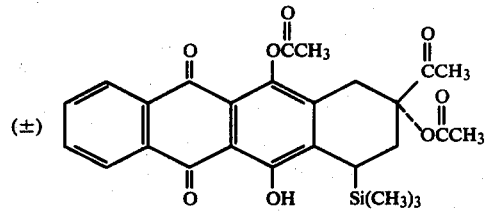

EXAMPLE 25

To a solution of 1.0 part by weight of lead tetraacetate in 25 parts by volume of acetic acid is added 0.5 part by volume of water and 0.32 part by weight of trans-(±)-9-acetyl-9,11-bis(acetyloxy)-7,8,9,10-tetrahydro-6-hydroxy-7-(trimethylsilyl)-5,12-naphthacenedione (XXVII). After 2 hours at room temperature the reaction is complete and the mixture is diluted with 250 parts by volume of water. The resulting precipitate is collected, washed with water and dried. The solid is extracted with methylene chloride filtering to remove the lead oxides. The solution is concentrated to a small volume and diluted with ethyl ether to give a solid which is recrystallized from methylene chloride-ethyl ether to yield pure cis-(±)-9-acetyl-7,9,11-tris(acetyloxy)-7,8,9,10-tetrahydro-6-hydroxy-5,12-naphthacenedione (XXVIII) which melts at 220°-223° C. and has the following structural formula

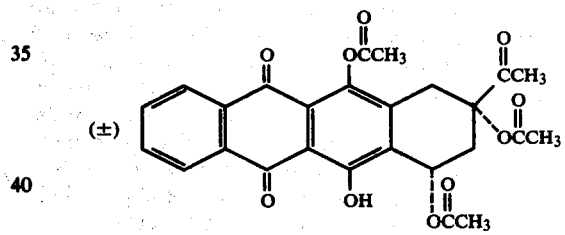

Chromatographic separation of the mother liquors on neutral silicic acid developing with 10% ethyl acetate in benzene gives two main fractions. The first fraction consists of a mixture containing about 25% of the above compound with about 75% of trans-(±)-9-acetyl-7,9,11-tris(acetyloxy)-7,8,9,10-tetrahydro-6-hydroxy-5,12-naphthacenedione which has the following structural formula

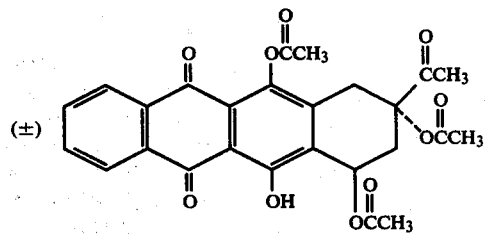

The second fraction consists of an approximately equal mixture of cis- and trans-(±)-9-acetyl-9,11-bis(acetyloxy)-7,8,9,10-tetrahydro-6,7-dihydroxy-5,12-naphthacenedione which have the following structural formulas

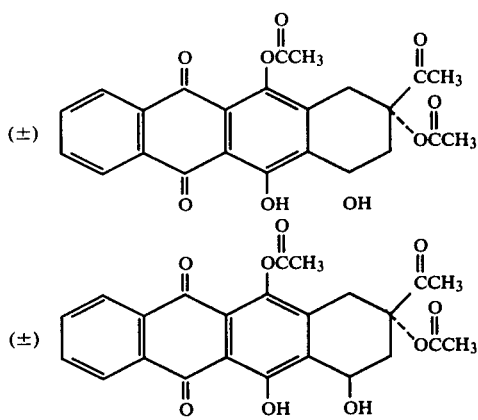

EXAMPLE 26

A round bottom flask containing a magnetic stirring bar is charged with 25 parts by volume of anhydrous ethanol. Argon is bubbled through the stirred solvent for 1 hour. The solvent is then refluxed for 1 hour under an argon atmosphere and cooled to room temperature. 0.1 Part by weight of (±)-3-(acetyloxy)-1,4,4aβ,12aβ-tetrahydro-6,11-dihydroxy-1α-(trimethylsilyl)-5,12-naphthacenedione (VII) is added to the flask producing a yellow heterogeneous mixture which is cooled to 0° C. in an ice bath. 0.34 Parts by volume methylmagnesium bromide in ethyl ether (2.15 M) is syringed into the stirred reaction mixture. After 45 minutes at 0° C. the homogeneous orange solution is poured into a mixture of 50 parts by volume of 2% acetic acid and 50 parts by volume of methylene chloride. The methylene chloride phase is separated and the aqueous phase extracted twice with 50 parts by volume of methylene chloride. The combined organic extracts are dried over anhydrous disodium sulfate, filtered and stripped on a rotary evaporator to give (±)-3,4,4aβ,12aβ-tetrahydro-6,11-dihydroxy-1α-(trimethylsilyl)-2,5,12(1H)-naphthacenetrione (IX) which has the following structural formula

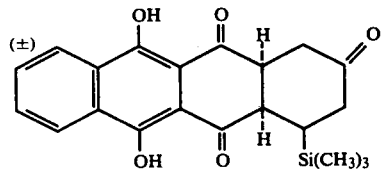

EXAMPLE 27

Substituting 5-hydroxy-1,4,9,10-anthracenetetrone for the 1,4,9,10-anthracenetetrone in Example 5 and substantially repeating procedures described in Examples 5 through 20 gives cis-(±)-9-acetyl-4-hydroxy-7,8,9,10-tetrahydro-6,7,9,11-tetrahydroxy-5,12-naphthacenedione also known as (±)-carminomycinone which has the following structural formula

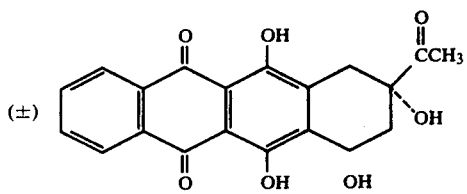

What we claim is:
1. A compound of the formula

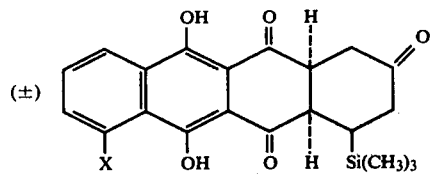

wherein X is hydrogen, methoxy, or hydroxy.

2. (±)-3,4,4aβ,12aβ-Tetrahydro-6,11-dihydroxy-4α-(trimethylsilyl)-2,5,12(1H)-naphthacenetrione.

3. (±)-3,4,4aβ,12aβ-Tetrahydro-6,11-dihydroxy-4α-(trimethylsilyl)-7-methoxy-2,5,12(1H)-naphthacenetrione.

4. A compound of the formula

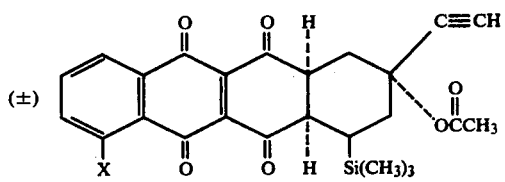

wherein X is hydrogen, methoxy, or hydroxy.

5. (±)-3β-(Acetyloxy)-3-ethynyl-1,2,3,4,4aβ,12aβ-hexahydro-1α-(trimethylsilyl)-5,6,11,12-naphthacenetetrone.

6. (±)-3β-(Acetyloxy)-3-ethynyl-1,2,3,4,4aβ,12aβ-hexahydro-1α-(trimethylsilyl)-10-methoxy-5,6,11,12-naphthacenetetrone.

7. A compound of the formula

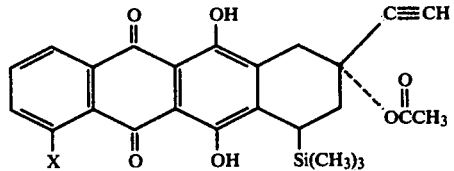

wherein X is hydrogen, methoxy, or hydroxy.

8. trans-(±)-9-(Acetyloxy)-9-ethynyl-7,8,9,10-tetrahydro-6,11-dihydroxy-7-(trimethylsilyl)-5,12-naphthacenedione.

9. trans-(±)-9-(Acetyloxy)-9-ethynyl-4-methoxy-7,8,9,10-tetrahydro-6,11-dihydroxy-7-(trimethylsilyl)-5,12-naphthacenedione.

* * * * *